United States Patent
Valcarce Lopez et al.

(10) Patent No.: US 10,980,861 B2
(45) Date of Patent: *Apr. 20, 2021

(54) GLUCOKINASE ACTIVATOR COMPOSITIONS FOR THE TREATMENT OF DIABETES

(71) Applicant: vTv Therapeutics LLC, High Point, NC (US)

(72) Inventors: Maria Carmen Valcarce Lopez, Oak Ridge, NC (US); Tung Fong, Somerset, NJ (US)

(73) Assignee: vTv Therapeutics LLC, High Point, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/744,956

(22) Filed: Jan. 16, 2020

(65) Prior Publication Data

US 2020/0138909 A1     May 7, 2020

Related U.S. Application Data

(63) Continuation of application No. 15/983,249, filed on May 18, 2018, now Pat. No. 10,588,943, which is a continuation of application No. 14/071,976, filed on Nov. 5, 2013, now Pat. No. 10,004,782, which is a continuation of application No. PCT/US2013/041076, filed on May 15, 2013.

(60) Provisional application No. 61/648,110, filed on May 17, 2012.

(51) Int. Cl.
| | |
|---|---|
| *A61K 38/26* | (2006.01) |
| *A61K 45/06* | (2006.01) |
| *A61K 31/426* | (2006.01) |
| *A61K 31/4985* | (2006.01) |
| *A61K 38/22* | (2006.01) |

(52) U.S. Cl.
CPC ........... *A61K 38/22* (2013.01); *A61K 31/426* (2013.01); *A61K 31/4985* (2013.01); *A61K 38/26* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 10,004,782 | B2* | 6/2018 | Valcarce Lopez | ........ A61P 9/00 |
| 10,588,943 | B2* | 3/2020 | Valcarce Lopez | ..... A61K 38/22 |
| 2007/0054897 | A1* | 3/2007 | Murray | ................ A61K 31/427 |
| | | | | 514/218 |
| 2008/0026987 | A1* | 1/2008 | Mackay | .................... A61P 3/10 |
| | | | | 424/400 |

OTHER PUBLICATIONS

Drucker "Sitagliptin," Nature Reviews, Drug Discovery, Feb 2007, vol. 6, pp. 109-110 (Year: 2007).*
Nathan ("Medical Management of Hyperglycemia in Type 2 Diabetes: A Consensus Algorithm for the Initiation and Adjustment of Therapy," Diabetes Care, Jan 2009, vol. 32, pp. 193-203 (Year: 2009).*
Davidson "Exenatide," Nature Reviews, Drug Discovery, Sept 2005, vol. 4, pp. 713-714 (Year: 2005).*
Ripsin "Management of Blood Glucose in Type 2 Diabetes Mellitus," American Family Physician, Jan 2009, vol. 79, pp. 29-36 (Year: 2009).*
Matschinsky "Research and Development of Glucokinase Activators for Diabetes Therapy: Theoretical and Practical Aspects" in M. Schwanstecher (ed.), Diabetes—Perspectives in Drug Therapy, Handbook of Experimental Pharmacology 203, 2011, pp. 357-401 (Year: 2011).*

* cited by examiner

*Primary Examiner* — Christina Bradley
(74) *Attorney, Agent, or Firm* — Samuel B. Rollins (57) ABSTRACT

The present invention relates to the use of liver-selective glucokinase activators and a GLP1 analog in restoring insulin sensitivity and treating type II diabetes, including reducing body weight in subjects undergoing type II diabetes treatment.

17 Claims, 6 Drawing Sheets

Specification includes a Sequence Listing.

FIGURE 1 b, group B vs A; c, group C vs A; d, group D vs A; e, group E vs A; f, group F vs A; ψ, group F vs D; +, group F vs C.

one symbol, $p<0.05$; 2 symbols, $p<0.01$; 3 symbols, $p<0.001$.

GLUCOKINASE ACTIVATOR COMPOSITIONS FOR THE TREATMENT OF DIABETES

FIELD OF THE INVENTION

The present invention relates to pharmaceutical compositions comprising {2-[3-cyclohexyl-3-(trans-4-propoxy-cyclohexyl)-ureido]-thiazol-5-ylsulfanyl}-acetic acid (FRI-1) in combination with an anti-diabetic drug selected from the group consisting of metformin, sitagliptin or exenatide. The present invention also relates to the use of the pharmaceutical compositions in restoring insulin sensitivity and treating type II diabetes, including reducing body weight in subjects undergoing type II diabetes treatment.

BACKGROUND OF THE INVENTION

Diabetes is a disorder characterized by impaired glucose metabolism manifested by an elevated glucose level in subjects. There are two forms of diabetes based on the underlying defects of the disease. Type I diabetes arises when subjects lack pancreatic β-cells producing insulin, the hormone that regulates glucose utilization. Type II diabetes arises when subjects have impaired β-cell function, including other abnormalities. In type II diabetic subjects, plasma insulin levels may be the same or even elevated compared to non-diabetic subjects. Such plasma insulin levels, while elevated, lead to impaired insulin-stimulated glucose uptake in muscles. Also, insulin-resistant adipocytes have diminished capacity to mobilize lipids and triglycerides. Consequently, an increase in circulating glucose and lipids is seen, leading to the metabolic abnormalities often associated with type II diabetes.

Type I subjects are currently treated with insulin. While the majority of type II subjects are treated with sulfonylureas or metformin, these subjects gradually lose the ability to respond to monotherapy, thus requiring treatment with multiple drugs.

An option for normalizing blood glucose levels is the use of combination therapies. For example, an FDA approved combination treatment of type II diabetes is the use of dipeptidyl peptidase-IV (DPP-IV) inhibitors with metformin. Another combination treatment currently under investigation uses glucokinase ("GK") activators in combination with metformin and is described in WO11/149945.

The long-term efficacy of therapies for type II diabetes is limited by the risk of developing side effects, for example, hypoglycemia and weight gain in subjects undergoing treatment. Accordingly, there is a need to find better options for treating type II diabetes, which include restoring insulin sensitivity and/or controlling weight gain in subjects undergoing such treatment.

SUMMARY OF THE INVENTION

The present invention provides for pharmaceutical compositions comprising one or more glucokinase activators and one or more anti-diabetic drugs, as well as their use in treating type 2 diabetes and related disorders.

In one aspect, the present invention provides for a pharmaceutical composition comprising a glucokinase activator, or a pharmaceutically acceptable salt thereof, an anti-diabetic drug selected from the group consisting of a DPP-IV inhibitor, a GLP-1 analog, or a pharmaceutically acceptable salt thereof; and at least one pharmaceutically acceptable carrier, excipient, diluent or mixture thereof. In some embodiments, the glucokinase activator, the anti-diabetic drug, or both are present in suboptimal amounts. The glucokinase activator can be a liver-selective glucokinase activator. In some embodiments, the glucokinase activator can be {2-[3-cyclohexyl-3-(trans-4-propoxy-cyclohexyl)-ureido]-thiazol-5-ylsulfanyl}-acetic acid or a pharmaceutically acceptable salt thereof. In other embodiments, the anti-diabetic drug is sitagliptin, exenatide, or a pharmaceutically acceptable salt thereof.

In another aspect, the present invention provides for a method of treating type II diabetes comprising administering to a subject a pharmaceutical composition comprising a glucokinase activator or a pharmaceutically acceptable salt thereof and an anti-diabetic drug selected from the group consisting of a DPP-IV inhibitor and a GLP-1 analog or a pharmaceutically acceptable salt thereof. In some embodiments, the glucokinase activator, the anti-diabetic drug, or both are present in suboptimal amounts. The glucokinase activator can be a liver-selective glucokinase activator. In some embodiments, the glucokinase activator can be {2-[3-cyclohexyl-3-(trans-4-propoxy-cyclohexyl)-ureido]-thiazol-5-ylsulfanyl}-acetic acid or a pharmaceutically acceptable salt thereof. In other embodiments, the anti-diabetic drug is sitagliptin, exenatide, or a pharmaceutically acceptable salt thereof.

In another aspect, the present invention provides for a method of improving glycemic control comprising administering to a subject a pharmaceutical composition comprising a glucokinase activator or a pharmaceutically acceptable salt thereof and an anti-diabetic drug selected from the group consisting of DPP-IV inhibitor and a GLP-1 analog or a pharmaceutically acceptable salt thereof.

In another aspect, the present invention provides for a method of treating a condition in a subject comprising administering to a pharmaceutical composition comprising a glucokinase activator or a pharmaceutically acceptable salt thereof and an anti-diabetic drug selected from the group consisting of DPP-IV inhibitor and a GLP-1 analog or a pharmaceutically acceptable salt thereof, wherein the condition is selected from the group consisting of a metabolic disorder, glucose intolerance, prediabetic state, insulin resistance, hyperglycemia, impaired glucose tolerance (IGT), Syndrome X, impaired fasting glucose (IFG), type I diabetes, dyslipidemia, hyperlipidemia, hyperlipoproteinemia, hypertension, osteoporosis, non-alcoholic fatty liver disease (NAFLD), complications resulting from or associated with diabetes, cardiovascular disease, and obesity.

In another aspect, the present invention provides for a method of normalizing or lowering blood glucose; delaying IGT to type II diabetes; delaying the progression of non-insulin-requiring type II diabetes to insulin-requiring type II diabetes; lowering of food intake; regulating appetite; regulating feeding behavior; enhancing secretion of enteroincretins; improving glucose tolerance; reducing fasting plasma glucose; reducing postprandial plasma glucose; reducing glycosylated hemoglobin HbA1c; slowing progression of, delaying or treating complications of diabetes; reducing weight or preventing an increase of weight or facilitating a reduction of weight; treating the degeneration of pancreatic beta cells; improving and/or restoring functionality of pancreatic beta cells; stimulating and/or restoring functionality of pancreatic insulin secretion; enhancing phosphorylation of glucose; maintaining insulin sensitivity; improving insulin sensitivity; treating hyperinsulinemia; or treating insulin resistance comprising administering to a subject a pharmaceutically acceptable salt thereof and an anti-diabetic drug selected from the group consisting of DPP-IV inhibitor and a GLP-1 analog or a pharmaceutically acceptable salt thereof.

Other features and aspects of the present invention are also described herein.

DETAILED DESCRIPTION OF THE INVENTION

I. Definitions

The term "GK activator" refers to a compound that sensitizes the glucokinase (GK) sensor system. GK is an enzyme that belongs to the family of hexokinases, which catalyze the first step in the metabolism of glucose, i.e., conversion of glucose to glucose-6-phosphate. GK functions as a glucose sensor in the pancreas and liver. In one embodiment, the GK activator is a liver selective activator that does not increase insulin secretion by the pancreas in presence of glucose. Exemplary GK activators include FRI-1 or those disclosed in WO05/066145. In one embodiment, a GK activator is FRI-1.

The term "FRI-1" is represented by the chemical name {2-[3-cyclohexyl-3-(trans-4-propoxy-cyclohexyl)-ureido]-thiazol-5-ylsulfanyl}-acetic acid. As used herein, FRI-1 is not limited to the free acid, but also includes pharmaceutically acceptable salts of FRI-1. In one embodiment, FRI-1 is a free acid.

The term "anti-diabetic drug" refers to agents found in the literature. As used herein, anti-diabetic drugs include pharmaceutically acceptable salts, pro-drugs, and pharmaceutically acceptable salts of pro-drugs of anti-diabetic drugs. Anti-diabetic drugs for example fall within the categories of insulin, insulin sensitizing active agents, active agents that enhance the production of insulin, sulfonamides, biguanidine derivatives and α-glucosidase inhibitors. Insulin, for example, is human insulin prepared by recombinant technology. The insulin sensitizing active agents enhance the effect of insulin, including, for example, PPAR (peroxisome proliferator-activated receptor) γ-agonists, including thiazolidinedione derivatives, such as pioglitazone, troglitazone, ciglitazone, rivoglitazone, rosiglitazone or other 2,4-thiazolidinedione derivatives. Active agents that enhance the production of insulin include, for example, DPP-IV inhibitors, such as sitagliptin, vildagliptin, saxagliptin, linagliptin, dutogliptin, gemigliptin or alogliptin; GLP-1 analogs, such as exenatide, liraglutide, taspoglutide, albiglutide, or lixisenatide; and ATP-sensitive potassium channel modulators, such as mitiglinide, repaglinide or nateglinide. Sulfonamides include, for example, sulfonylurea derivatives, such as tolbutamide, chlorpropamide, tolazamide, acetohexamide, glipizide, gliclazide, glimepiride, gliquidone, glibornuride, glisoxepid, glibenclamide, glisentide, glisolamide, glybuzole, or glyclopyramide. Biguanidine derivatives include, for example, metformin, buformin, or phenformin. α-glucosidase inhibitors include, for example, miglitol, acarbose or voglibose. In one embodiment, an anti-diabetic drug may be included in any dosage form, e.g., oral, inhaled or an injectable dosage form. In another embodiment, an anti-diabetic drug is in an oral dosage form.

The term "metformin" is represented by the chemical name, N,N-dimethylimidodicarbonimidic diamide. As used herein, metformin is not limited to the free base, but also includes pharmaceutically acceptable salts of metformin. In one embodiment, metformin is metformin hydrochloride.

The term "DPP-IV inhibitor" means a compound that inhibits the action of dipeptidyl peptidase IV from cleaving dipeptides located at N-terminal portions of proteins having either an N-terminal proline or alanine residue. In one embodiment, a DPP-IV inhibitor is sitagliptin.

The term "sitagliptin" is represented by the chemical name, (3R)-3-amino-1-[3-(trifluoromethyl)-5,6,7,8-tetrahydro-5H-[1,2,4-]triazolo[4,3-a]pyrazin-7-yl]-4-(2,4,5-trifluorophenyl)butan-1-one. As used herein, sitagliptin is not limited to the free base, but also includes pharmaceutically acceptable salts of sitagliptin, and isomers of sitagliptin. In one embodiment, sitagliptin is sitagliptin phosphate.

The term "GLP-1 analog" means a glucagon-like peptide-1 compound having sequence similarity of about 30% to about 90%, or about 40% to about 75% to glucagon like peptide-1 (also referred to as pro-glucagon). GLP-1 has an insulinotropic effect, stimulating insulin secretion from pancreatic beta cells. In one embodiment, a GLP-1 analog is exenatide.

The term "exenatide" represents a 39-amino acid peptide with sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$ (SEQ. ID. No: 1). As used herein, exenatide is not limited to the free base, but also includes pharmaceutically acceptable salts of exenatide. In one embodiment, exenatide is a free base.

The term "pharmaceutically acceptable salt" represents those salts which are suitable for use in contact with the tissues of humans and lower animals without undue toxicity, irritation, allergic response and the like, and are commensurate with a reasonable benefit/risk ratio. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, DIPEAtes, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxyethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates. In one embodiment, the pharmaceutically acceptable salt can be a hydrochloride, a hydrobromide, a hydroformate, or a maleate salt.

The term "in combination" means a pharmaceutical composition that places no limit, i.e., method, form, etc., on the administering of a compound in combination with another compound. For example, in some embodiments, FRI-1 and an anti-diabetic drug are administered together in a single dosage form, e.g., fixed dose combination. In other embodiments, FRI-1 and an anti-diabetic drug are administered in separate, discrete dosage forms e.g., one may be an oral preparation and the other may be an inhaled dose form, or as same dosage forms, or in separate containers, e.g., blisters. In another embodiment, both FRI-1 and an anti-diabetic drug are administered at the same time or are taken sequentially administered about 5 minutes apart, or about 15 minutes apart, or about 30 minutes apart, or about 1 hour apart, or about 2 hours apart, or about 4 hours apart, or about 8 hours apart, or about 12 hours apart, or about 24 hours apart, wherein FRI-1 is administered earlier than the anti-diabetic drug, or vice versa.

The term "treating or treatment" means to manage or control a disease, condition or disorder. This includes relieving, alleviating, ameliorating, delaying, reducing, reversing, or improving a disease, disorder or condition or at least one symptom thereof; delaying the onset of a disease, disorder, or condition; or delaying the recurrence of a disease, disorder, or condition, or characteristic symptoms thereof, depending on the nature of the disease, disorder, or condition and its characteristic symptoms.

The term "subject" means animals, including both males and females. In one embodiment, subject means mammals. In another embodiment, subject means humans.

The term "therapeutic effect" means an amount of an active ingredient (e.g., GK activator or an anti-diabetic drug) that elicits the biological or medicinal response in a tissue, system, or subject that is being sought by a researcher, veterinarian, medical doctor, patient or other clinician, which includes reduction or alleviation of the symptoms of the disease being treated.

The term "glycemic control" means the management of diabetes as measured by the diagnostic parameters or HbA1c and/or FPG. Subjects with inadequate or insufficient glycemic control include subjects having a HbA1c value from about 7.5% to about 15% at baseline, from about 8% to about 13% at baseline, and from about 9% to about 12% at baseline. In one embodiment, subjects with inadequate glycemic control include subjects having a HbA1c value from 7.5% to about 10% at baseline despite treatment with metformin.

As used herein, the term "consisting of" is not an absolute restriction and includes unrecited components. Typically, the unrecited components include an impurity ordinarily associated therewith or a component unrelated to the invention.

II. Pharmaceutical Compositions

In one embodiment, the present invention provides a pharmaceutical composition comprising a GK activator in combination with an anti-diabetic drug, and at least one pharmaceutically acceptable carrier, diluent or excipient. In one embodiment, the pharmaceutically acceptable carriers are present in two discrete dosage forms, one dosage form comprising a GK activator and the other dosage form comprising an anti-diabetic drug. In another embodiment, the active ingredients of the combination are combined in a single dosage form. In yet another embodiment, the dosage form is intended for oral use. In another embodiment, the pharmaceutical composition consists of a GK activator and an anti-diabetic drug.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example, magnesium stearate, stearic acid or talc.

In another embodiment, the present invention provides a pharmaceutical composition comprising FRI-1 or a pharmaceutically acceptable salt thereof in combination with an anti-diabetic drug wherein the anti-diabetic drug is selected from the group consisting of metformin, sitagliptin and exenatide, or a pharmaceutically acceptable salt thereof.

In another embodiment, the present invention provides a pharmaceutical composition comprising FRI-1 or a pharmaceutically acceptable salt thereof in combination with metformin or a pharmaceutically acceptable salt thereof.

In another embodiment, the present invention provides a pharmaceutical composition comprising FRI-1 or a pharmaceutically acceptable salt thereof in combination with sitagliptin or a pharmaceutically acceptable salt thereof.

In another embodiment, the present invention provides a pharmaceutical composition comprising FRI-1 or a pharmaceutically acceptable salt thereof in combination with exenatide or a pharmaceutically acceptable salt thereof.

We have surprisingly found that the administration of FRI-1 in combination with metformin, sitagliptin or exenatide is synergistic in the context of modifying glucose metabolism in subjects in need of such modification. In another embodiment, we have surprisingly found that the administration of FRI-1 in combination with sitagliptin is synergistic in controlling body weight in subjects having impaired glucose metabolism. Further, we have surprisingly found that the administration of FRI-1 in combination with exenatide is synergistic in the context of improving insulin sensitivity in subjects with impaired glucose metabolism. Additionally we have surprisingly found the administration of FRI-1 in combination with metformin is synergistic both in the context of controlling body weight in subjects with impaired glucose metabolism as well as improving insulin sensitivity in subjects with improved glucose metabolism. In one embodiment, the present invention provides for small doses of either FRI-1 or an anti-diabetic drug or both, wherein the small doses are such that they are less than the optimum dose of either FRI-1 or anti-diabetic drug for a therapeutic effect. In another embodiment, small doses of either active ingredient of the present invention are administered simultaneously or sequentially in any order.

Pharmaceutical compositions can be prepared by methods known by one of ordinary skill in the art, including the selection of pharmaceutically acceptable ingredients.

In one embodiment, the present invention provides for a pharmaceutical composition that is an oral dosage form administered as discrete solid units, e.g., capsules, tablets, pills, powders, granules etc. Oral dosage forms can include any pharmaceutical carrier, diluents (such as sucrose, mannitol, lactose, starches) or excipients known in the art, including but not limited to suspending agents, solubilizers, buffering agents, binders, disintegrants, preservatives, colorants, flavorants, lubricants may be used. In some embodiments, the present invention provides an oral dosage form for either or both of GK activator and anti-diabetic drug.

In another embodiment, the present invention provides for a pharmaceutical composition that is an oral dosage administered as a liquid form. Exemplary liquid oral dosage forms are aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention.

In yet another embodiment, the present invention provides for a pharmaceutical composition that is an injectable dosage form, for example, intravenously, in the form of an isotonic sterile solution. In yet another embodiment, the present invention provides an injectable dosage form for either or both of GK activator and anti-diabetic drug.

In another embodiment, the present invention provides for a pharmaceutical composition that is an inhalable dosage form, for example in the form of a powder (e.g., micronized) or in the form of atomized solutions or suspensions. In yet another embodiment, the present invention provides an inhalable dosage form for either or both of GK activator and anti-diabetic drug.

In some embodiments, the pharmaceutical composition is a single dosage form comprising one or more GK activators and one or more anti-diabetic drugs. In other embodiments, two or more dosage forms are provided, where at least one dosage form comprises one or more GK activators and at least one other dosage form comprises one or more anti-diabetic drug.

III. Dosage Quantities

The dosage of the pharmaceutical composition of the present invention will vary depending on the symptoms, the treatment desired, age and body weight of the subject, the nature and severity of the disorder to be treated, the route of administration and pharmacokinetics of the active ingredients. The frequency of the dose indicated will also vary with the treatment desired and the disorder indicated.

In one embodiment, a GK activator is administered in combination with an anti-diabetic drug in an amount sufficient to achieve a therapeutic effect. The dosage range for a GK activator ranges from about 1 mg to about 1000 mg per day. In other embodiments, the amount for a GK activator ranges from about 5 mg to about 900 mg per day, or about 10 mg to about 800 mg per day, or about 50 mg to about 700 mg per day, or about 150 mg to about 500 mg per day, or about 200 mg to about 400 mg per day. The dosage range for an anti-diabetic drug ranges from about 0.1 µg to about 2000 mg per day. In other embodiments, the amount for an anti-diabetic drug ranges from about 0.5 µg to about 1000 mg per day, or about 1 µg to about 750 mg per day, or about 5 µg to about 500 mg per day, or about 20 µg to about 250 mg per day, or about 100 µg to about 100 mg per day, or about 500 µg to about 10 mg per day, or about 1 mg to about 5 mg per day.

In yet other embodiments, the dosage of FRI-1 is about 0.05 mg/kg of body weight per day, or about 0.1 mg/kg of body weight per day, or about 0.3 mg/kg of body weight per day, or about 1 mg/kg of body weight per day or about 5 mg/kg of body weight per day, or about 25 mg/kg of body weight per day, or about 100 mg/kg of body weight per day, or about 200 mg/kg of body weight per day or about 500 mg/kg of body weight per day; and the dosage for anti-diabetic drugs, wherein the anti-diabetic drug is selected from the group consisting of metformin, sitagliptin, and exenatide, is about 0.005 mg/kg of body weight per day, or about 0.01 mg/kg of body weight per day, or about 0.05 mg/kg of body weight per day, or about 0.1 mg/kg of body weight per day, or about 0.3 mg/kg of body weight per day, or about 1 mg/kg of body weight per day or about 5 mg/kg of body weight per day, or about 25 mg/kg of body weight per day, or about 100 mg/kg of body weight per day, or about 200 mg/kg of body weight per day or about 500 mg/kg of body weight per day. One skilled in the art will appreciate that the administered doses can be converted to a human equivalent dose.

Metformin is known to one skilled in the art and may be administered as a monotherapy in an amount of 500 mg per day to 2550 mg per day, typically in the form of 500 mg, 850 mg and 1000 mg tablets. In smaller, suboptimal doses, metformin may offer no or negligible therapeutic benefits when administered as a monotherapy. Metformin can be administered in suboptimal doses, in combination with a GK activator, and provide a therapeutic benefit (for example, less than 500 mg daily). Metformin can also be administered in optimal doses, in combination with a GK activator, and provide a synergistic therapeutic benefit. In some embodiments, the administered dose of metformin can be from about 100 mg to about 2600 mg per day, or from about 250 mg to about 2500 mg per day, or from about 500 mg to about 1500 mg per day, or from about 250 mg to about 1000 mg per day, or from about 350 mg to about 850 mg per day, or from about 400 mg to about 750 mg per day. In other embodiments, the administered dose of metformin is less than 500 mg per day, for example, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg or 475 mg per day.

Sitagliptin is known to one skilled in the art and may be administered as a monotherapy in an amount of 100 mg per day, while in patients with moderate, severe and end stage renal disease the administered amount may be 25 mg or 50 mg per day. In smaller, suboptimal doses, sitagliptin may offer no or negligible therapeutic benefits when administered as a monotherapy. Sitagliptin can be administered in suboptimal doses, in combination with a GK activator, and provide a therapeutic benefit (for example, less than 100 mg daily is a suboptimal amount for patients without renal disease, and less than 25 mg daily is a suboptimal amount for patients with renal disease). Sitagliptin can also be administered in optimal doses, in combination with a GK activator, and provide a synergistic therapeutic benefit. In some embodiments, the administered dose of sitagliptin ranges from about 0.1 mg to about 500 mg per day administered orally. In other embodiments, the amount of sitagliptin ranges from about 0.25 mg to about 400 mg per day, or from about 0.5 mg to about 250 mg per day, or from about 1 mg to about 100 mg per day, or from about 5 mg to about 50 mg per day, or from about 10 mg to about 25 mg per day. In other embodiments, the amount of sitagliptin is less than 100 mg per day, for example, 25 mg, 30 mg, 35 mg, 40 mg, 45 mg, 50 mg, 55 mg, 60 mg, 65 mg, 70 mg, 75 mg, 80 mg, 85 mg, 90 mg or 95 mg per day. In yet other embodiments, the amount of sitagliptin is less than about 25 mg per day, for example, about 0.1 mg, 0.5 mg, 1 mg, 2 mg, 3 mg, 4 mg, 5 mg, 7.5 mg, 10 mg, 12.5 mg, 15 mg, 17.5 mg, 20 mg or 22.5 mg per day.

Exenatide is known to one skilled in the art and can be administered as a monotherapy in an amount of 10 µg to 20 µg per day or 2 mg per week. In smaller, suboptimal doses, exenatide may offer no or negligible therapeutic benefits when administered as a monotherapy. Exenatide can be administered in suboptimal doses, in combination with a GK activator, and provide a therapeutic benefit (for example, less than 500 mg daily). Exenatide can also be administered in optimal doses, in combination with a GK activator, and provide a synergistic therapeutic benefit. In one embodiment, the dose of exenatide is 0.1 µg to about 100 µg per day administered subcutaneously. In other embodiments, the amount of exenatide ranges from about 0.25 µg to about 75 µg per day, from about 0.5 µg to about 50 µg per day, from about 1 µg to about 25 µg per day, or from 5 µg to about 10 µg per day. In other embodiments, the amount of exenatide is less than about 10 µg per day, for example, about 0.25 µg, 0.5 µg, 1 µg, 1.5 µg, 2 µg, 2.5 µg, 3 µg, 3.5 µg, 4 µg, 4.5 µg, 5 µg, 5.5 µg, 6 µg, 6.5 µg, 7 µg, 7.5 µg, 8 µg, 8.5 µg, 9 µg or 9.5 µg per day.

IV. Methods of Treatment

In one embodiment, the present invention provides for treating subjects comprising administering to a subject in need thereof a pharmaceutical composition comprising a GK activator in combination with an anti-diabetic drug for the following methods:
(a) treating type I diabetes and/or type II diabetes.
(b) normalizing or lowering blood glucose levels;
(c) improving glucose tolerance;
(d) improving glycemic control;
(e) reducing fasting plasma glucose;
(f) reducing postprandial plasma glucose
(g) reducing glycosylated hemoglobin HbA1c;
(h) slowing progression of, delaying or treating complications of diabetes, e.g., diabetic nephropathy, retinopathy, neuropathy or cardiovascular disease;
(i) reducing weight or preventing an increase of weight or facilitating a reduction of weight;
(j) treating the degeneration of pancreatic beta cells;
(k) improving and/or restoring functionality of pancreatic beta cells;
(l) stimulating and/or restoring functionality of pancreatic insulin secretion;
(m) enhancing phosphorylation of glucose; or
(n) maintaining and/or improving insulin sensitivity; and/or treating hyperinsulinemia and/or insulin resistance.

In one embodiment, the present invention provides for normalizing blood glucose levels and improving glucose tolerance in a subject by administering to the subject a pharmaceutical composition comprising FRI-1 or a pharmaceutically acceptable salt thereof in combination with an anti-diabetic drug, wherein the anti-diabetic drug is selected from the group consisting of metformin, sitagliptin and exenatide or a pharmaceutically acceptable salt thereof.

In another embodiment, the present invention provides for improving glycemic control; and/or for reducing fasting plasma glucose, reducing postprandial plasma glucose and/or reducing glycosylated hemoglobin HbA1c in a subject by administering to the subject a pharmaceutical composition comprising FRI-1 or a pharmaceutically acceptable salt thereof in combination with an anti-diabetic drug, wherein the anti-diabetic drug is selected from the group consisting of metformin, sitagliptin and exenatide or a pharmaceutically acceptable salt thereof. In an embodiment, a method may reduce the amount of HbA1c in a subject in need thereof by at least 0.1 of a percentage point, or 0.2 of a percentage point, or 0.3 of a percentage point, or 0.4 of a percentage point, or 0.5 of a percentage point, or 0.6 of a percentage point, or 0.7 of a percentage point, or 0.8 of a percentage point, or 0.9 of a percentage point, or one percentage point. In still other embodiments, the method may reduce the level of HbA1c in a subject in need thereof to less than 7%. In other embodiments, the level of HbA1c may be reduced to a level between 5 and 6.5%.

In another embodiment, the present invention provides for slowing progression of, delaying or treating complications in a subject (e.g., diabetic nephropathy, retinopathy, neuropathy or cardiovascular disease) by administering to the subject a pharmaceutical composition comprising FRI-1 or a pharmaceutically acceptable salt thereof in combination with an anti-diabetic drug, wherein the anti-diabetic drug is selected from the group consisting of metformin, sitagliptin and exenatide or a pharmaceutically acceptable salt thereof.

In yet another embodiment, the present invention provides for reducing weight or preventing an increase of weight or facilitating a reduction of weight in a subject by administering to the subject a pharmaceutical composition comprising FRI-1 or a pharmaceutically acceptable salt thereof in combination with an anti-diabetic drug, wherein the anti-diabetic drug is selected from the group consisting of metformin, sitagliptin and exenatide or a pharmaceutically acceptable salt thereof.

In another embodiment, the present invention provides for treating the degeneration of pancreatic beta cells; and/or improving and/or restoring functionality of pancreatic beta cells; and/or stimulating and/or restoring functionality of pancreatic insulin secretion in a subject by administering to the subject a pharmaceutical composition comprising FRI-1 or a pharmaceutically acceptable salt thereof in combination with an anti-diabetic drug, wherein the anti-diabetic drug is selected from the group consisting of metformin, sitagliptin and exenatide or a pharmaceutically acceptable salt thereof.

In another embodiment, the present invention provides for maintaining and/or improving insulin sensitivity; and/or treating hyperinsulinemia and/or insulin resistance in a subject by administering to the subject a pharmaceutical composition comprising FRI-1 or a pharmaceutically acceptable salt thereof in combination with an anti-diabetic drug, wherein the anti-diabetic drug is selected from the group consisting of metformin, sitagliptin and exenatide or a pharmaceutically acceptable salt thereof. In yet another embodiment, the present invention provides for decreasing the daily dose of insulin by administering to a subject a pharmaceutical composition comprising FRI-1 or a pharmaceutically acceptable salt thereof in combination with an anti-diabetic drug, wherein the anti-diabetic drug is selected from the group consisting of metformin, sitagliptin and exenatide or a pharmaceutically acceptable salt thereof.

In yet another embodiment, the present invention provides for treating a condition in a subject comprising administering to the subject a GK activator in combination with an anti-diabetic drug, wherein the condition is selected from metabolic disorders (including metabolic syndrome), glucose intolerance, prediabetic state, insulin resistance, blood glucose lowering, hyperglycemia, impaired glucose tolerance (IGT), Syndrome X, impaired fasting glucose (IFG), type II diabetes, type I diabetes, delaying IGT to type II diabetes, delaying the progression of non-insulin-requiring type II diabetes to insulin-requiring type II diabetes, dyslipidemia, hyperlipidemia, hyperlipoproteinemia, hypertension, osteoporosis, non-alcoholic fatty liver disease (NAFLD), complications resulting from or associated with diabetes, (including nephropathy, retinopathy, neuropathy, impaired wound healing)) cardiovascular disease (including arteriosclerosis, atherosclerosis), lowering of food intake, appetite regulation, obesity, regulating feeding behavior, and enhancing secretion of enteroincretins.

In yet another embodiment, treatment of type II diabetes includes administering smaller doses, i.e., less than the optimum dose of either GK activator or anti-diabetic drug, or both until a therapeutic effect is attained. In smaller doses, either GK activator or anti-diabetic drug will offer negligible therapeutic benefits when administered alone. In yet another embodiment, the GK activator in combination with an anti-diabetic drug is administered simultaneously or sequentially to attain the desired therapeutic effect.

In other embodiments, the present invention provides for methods of treatment described herein as an adjunct to diet and exercise in subjects with type II diabetes or type I diabetes.

The invention will now be described in greater detail by reference to the following non-limiting examples.

EXAMPLES

Pharmacology

The efficacy of GK activators combined with metformin, sitagliptin or exenatide was examined on different functional end points, e.g., body weight or food intake or glucose tolerance or plasma fasting or fed glucose or plasma insulin or insulin sensitivity index in an in vivo model, e.g., ob/ob mice, relevant to the genetic mechanism over type II diabetes.

Fifty male ob/ob mice (approximately 6 weeks of age) were obtained from Charles River, Italy. Mice were singly housed in polypropylene cages with free access to a standard diet (Harlan Teklad Global 2018 diet) and tap water at all times. All animals were maintained at 24±2° C. and 55±20% humidity on a reverse phase 16 h on/8 h off light-dark cycle (lights on approximately 17:30-9:30 h).

Animals were acclimatized to the animal facility for two weeks. The following week (i.e., week 3), animals began a daily handling protocol (animals were handled as if to be dosed but were actually not weighed or dosed). Subsequent to the week-long handling protocol, animals were dosed with vehicle orally once daily for a 7 day baseline period (Day −6 to 0), i.e., dosing was three weeks after arrival of the animals in the facility. Dosing began at 08:45 each day so that approximately half of the animals were dosed prior to lights off and half after lights off (09:30). Body weight and food and water intake were recorded daily. During the baseline phase (Day −6) animals underwent blood sampling from the lateral tail vein (20 µL) with the sample taken into a lithium heparin-coated tube (Sarstedt CB300LH), i.e., a sample taken from freely feeding animals. Blood sampling began at approximately 16:00 to a timed schedule and food was removed immediately after sampling each animal. The following morning, 16 hours after the previous sample, a further (fasted) blood sample (20 µL) was taken from the lateral tail vein into a lithium heparin-coated collection tube (Sarstedt CB300LH). Food was replaced immediately after sampling and the animal was dosed. All blood samples were spun in a centrifuge immediately after collection and the plasma fraction stored frozen (−80° C.) prior to determining plasma glucose (duplicate) and insulin (single replicate) using commercially available kits and reagents: Alpco mouse ultrasensitive insulin kit 80-INSMSU-E10; Thermo Scientific Infinity glucose reagent TR15421.

Subsequently, baseline treatment continued. Towards the end of the baseline phase, animals were allocated into 6 treatment groups on the basis of body weight, baseline food and water intake, and fasted plasma glucose and insulin. Mice were dosed once daily orally (approximately 10 weeks of age at the first dose) for 14 days with vehicle or test drug as detailed in Table 1 below.

TABLE 1

| Group | Treatment (po; qd) | n |
|---|---|---|
| A | Vehicle | 8 |
| B | FRI-1 (25 mg/kg po) | 8 |
| C | FRI-1 (75 mg/kg po) | 8 |
| D | Metformin (100 mg/kg po) | 9 |
| E | FRI-1 (25 mg/kg po) + Metformin (100 mg/kg po) | 8 |
| F | FRI-1 (75 mg/kg po) + Metformin (100 mg/kg po) | 8 |

All treatments were dosed orally by gavage once daily. During the treatment period food intake, water intake and body weight was recorded daily at the dosing session. At the completion of dosing, animals were examined and any overt behavior was recorded. Dosing began at approximately 08:45 each day for all groups. On Days 6 and 7, blood samples were collected as described previously during the baseline phase. Hence, animals underwent blood sampling in the fed state at 16:00 on Day 6. Subsequently food was removed from each animal. The following morning, a further blood sample was taken (fasted state). This blood sample was timed such that it was taken 16 hours after the previous sample. Food was returned and the animal was dosed. On each occasion, approximately 20 µL blood was taken into a lithium heparin-coated tube (Sarstedt Microvette CB300LH). Each sample was centrifuged immediately and plasma dispensed into an aliquot tube. All plasma samples were frozen at −80° C. and subsequently assayed for glucose (n=2) and insulin (n=1) content using commercially available kits and reagents: Alpco mouse ultrasensitive insulin kit 80-INSMSU-E10; Thermo Scientific Infinity glucose reagent TR15421.

On day 13, animals underwent blood sampling in the freely fed state (at 16:00) as previously described and food was removed subsequent to sampling. On Day 14, the mice underwent an OGTT. Each animal was dosed with vehicle or test compound and 60 minutes later was dosed with D-glucose (2 g/kg po). Baseline blood samples were taken immediately prior to compound dosing (B1) and immediately before the glucose load (B2). Further blood samples were taken 10, 20, 30, 45, 60 and 120 minutes post glucose administration. All blood samples (all approximately 20 µL) were taken from the tail vein. Blood samples were taken into lithium heparinised tubes (Sarstedt Microvette CB300LH)

and plasma separated by centrifugation. All plasma samples were frozen at −80° C. and subsequently assayed for glucose (n=2) and insulin (n=1) content using commercially available kits and reagents: Alpco mouse ultrasensitive insulin kit 80-INSMSU-E10; Thermo Scientific Infinity glucose reagent TR15421. Animals were terminated subsequent to completion of the OGTT.

Evaluation of exenatide was conducted similar to the evaluation of metformin.

Evaluation of FRI-1 with or without sitagliptin was conducted in female diet induced obese rats. Sixty-eight dietary-induced obese, female Wistar rats (weight range 250-300 g) were obtained from Charles River (Margate, Kent) and housed in pairs in polypropylene cages with solid floors and sawdust bedding at a temperature of 21±4° C. and 55±20% humidity. Animals were maintained on a reverse phase light-dark cycle (lights off for 8 h from 09.30 17.30 h) during which time the room was illuminated by red light. Animals had free access to powdered high fat diet (VRF1 plus 20% lard), ground chocolate, ground peanuts and tap water at all times. The three different diets were contained in separate glass feeding jars with aluminum lids (Solmedia Laboratory Suppliers, Romford, Essex). Each lid had a hole cut in it to allow access to the food. Animals were housed in pairs for at least 14 weeks for the induction of obesity. Other experimental procedures for rats were similar to those for ob/ob mice.

Drugs and Dosing

Animals were dosed with 1% carboxymethylcellulose (Sigma C4888; Lot 120M0216V) vehicle for the first 5 days of the baseline phase. For the final two days of the baseline phase, animals were dosed with a vehicle of 20% gelucire (Gattefosse; Lot 103201) in distilled water. FRI-1 was stored refrigerated in a desiccator upon arrival and until use. Metformin was purchased from Sigma (catalog # D150959; Lot BCBF1484V). Exenatide was purchased from American Peptide (catalog #46-3-12B; Lot Y10049A1). Sitagliptin phosphate was purchased from Tocris Cookson, UK (Lot TCS9133B). The appropriate volume of vehicle (20% gelucire in distilled water) was added directly to the vial containing a weighed amount of drug material. The compound was vortexed for 10 seconds and was dosed at room temperature. Drug mixtures (i.e., groups E and F) were administered as a single dosing bolus. The appropriate volume of vehicle (20% gelucire in distilled water) was added directly to a vial containing a weighed amount of both FRI-1 and metformin. The resulting formulation was vortexed for 10 seconds and was dosed at room temperature. Drugs were formulated each day immediately prior to dosing and were administered using a dose volume of 2.5 mL/kg. D-Glucose was administered in the volume 2.5 mL/kg.

Data Analysis

Body weight and overall and weekly body weight gains (g) were determined by analysis of covariance with day 1 body weight as a covariate. Food and cumulative food intake (g) were determined by analysis of covariance with average daily food intake during the baseline phase (Days −6 to 0) as a covariate. Average food intake was determined using the same methods. Water intake (g) was determined by a robust regression model using M estimation and Huber weighting, using the default parameter c=1.345. The model had treatment as a factor and average daily water intake during the baseline phase (Days −6 to 0) as covariate. Average water intake was analyzed using the same method. Multiple comparisons against the vehicle group were by Williams' test for FRI-1, the multiple t test for Metformin and Dunnett's test for the combination of FRI-1 with metformin. The combination of FRI-1 and metformin was compared to metformin alone by Williams' test and to FRI-1 alone by the multiple t test. Plasma glucose and insulin data were analyzed by robust regression with treatment as a factor and bleeding order, baseline body weight, plasma glucose and insulin as covariates, followed by appropriate comparisons (two-tailed) to determine significant differences from the control group. The statistical methods assume that data are normally distributed with equal variance in the groups. Initial Shapiro-Wilk tests for normality of residuals showed that log (glucose) and log(insulin) were more normally distributed than glucose and insulin, so a log transformation was used. However, some Shapiro-Wilk tests were significant, so robust regression was used to downweight any possible outliers in the analysis of these variables.

For the OGTT, the treatment groups were compared at each post-dose time and by the area under the curves (AUC) for 0-60 minutes and 0-120 minutes ($AUC_{60\ min}$ and $AUC_{120\ min}$ respectively). These were calculated as:

$$AUC_{120\ min} = \frac{1}{24}(2t_{0\ min} + 4t_{10\ min} + 4t_{20\ min} + 5t_{30\ min} + 6t_{45\ min} + 15t_{60\ min} + 12t_{120\ min})$$

$$AUC_{60\ min} = AUC_{120\ min} - \frac{1}{2}(t_{60\ min} + t_{120\ min})$$

The AUCs above B2 baselines (AUCB2) were calculated as $AUC_{120\ min} - 2t_{0\ h}$ and $AUC_{60\ min} - t_{0\ h}$. In the above equations, t represents glucose or insulin concentration at a specific time indicated by the subscript. A log transformation was used, apart from the AUCBs, which can be negative, so these were not transformed. Analysis of the OGTT was by robust regression model using M estimation, Huber weighting, using the default parameter c=1.345. The model included treatment and assay day as factors and bleeding order, Day 1 body weight and Day −5 (fasted) baseline plasma log(glucose) or log(insulin) as covariates. For the AUCBs, untransformed Day −5 glucose or insulin was used as a covariate instead of log(glucose) or log(insulin). Fasted plasma glucose and insulin data on Day 7 were log transformed and analyzed by robust regression with treatment as a factor and bleeding order, Day 1 body weight and Day −5 (fasted) baseline plasma log(glucose) or log(insulin) as covariates. Unfasted plasma glucose and insulin data on Day 6 and 13 were log transformed and analyzed by robust regression with treatment as a factor and bleeding order, Day 1 body weight and Day −6 (unfasted) baseline plasma log(glucose) or log(insulin) as covariates. Comparisons against vehicle were by Williams' test for FRI-1, the multiple t test for metformin and Dunnett's test for the combination. The combination treatments were compared to metformin by Williams' test and to the same dose of FRI-1 by the multiple t test. P<0.05 was the level accepted for statistical difference. The chance of a false positive is 5% for each compound for each time. Tests were carried out as two-sided tests.

Results of Body Weight Studies with a FRI-1/Metformin Combination

Figure 1:
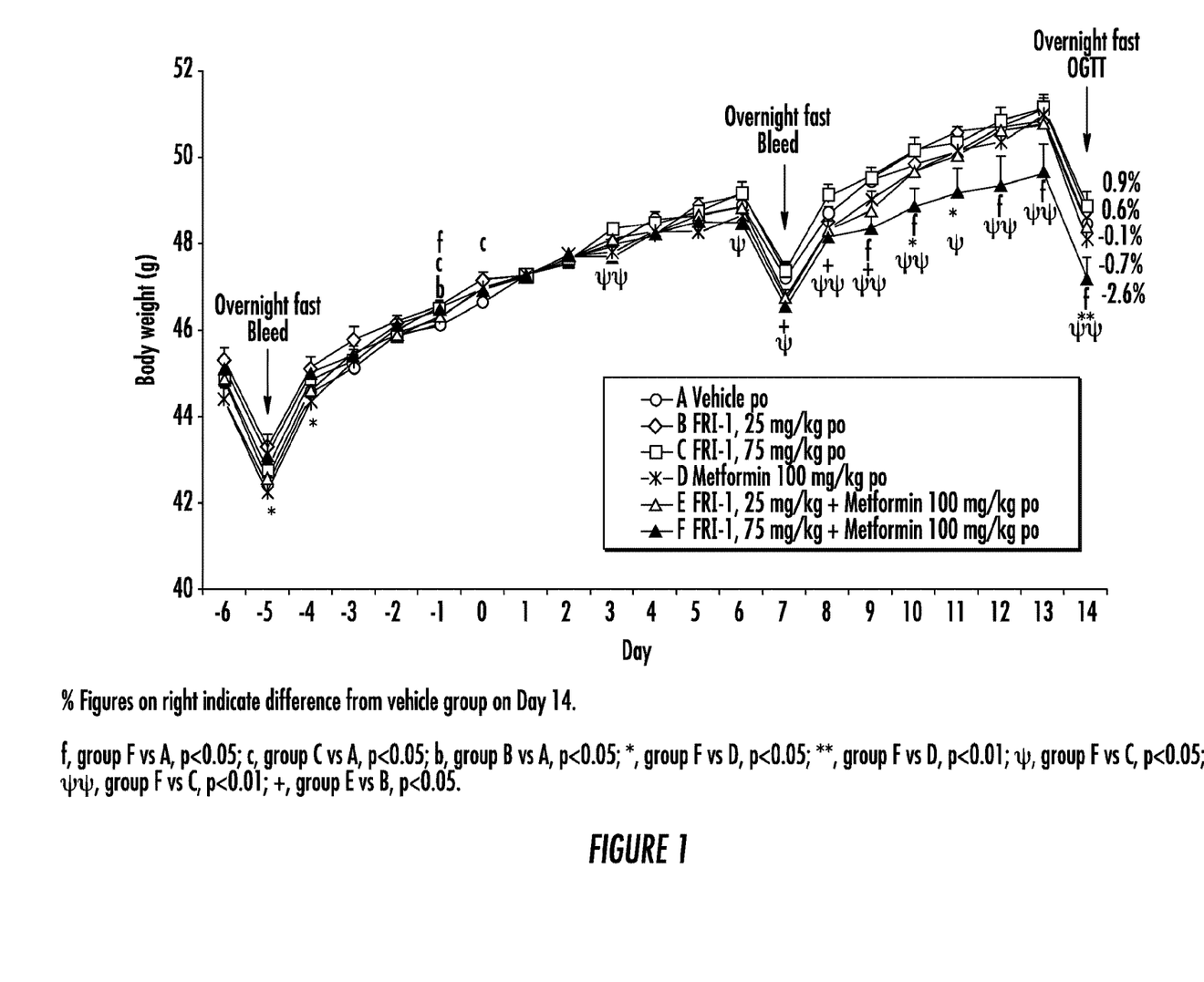
FIG. 1 depicts synergistic effects of a combination of FRI-1 and metformin on body weight reduction in male ob/ob mice.

The chronic administration of FRI-1 and metformin showed a synergistic effect on controlling body weight in male ob/ob mice as shown in FIG. 1. Once daily treatment with the combination of FRI-1 (75 mg/kg po) and metformin (100 mg/kg po) significantly reduced body weight (p>0.05) on Days 9, 10, 12, 13, and 14 of the study compared to vehicle-treated controls. No other drug treatment had a statistically significant effect on body weight during the dosing phase of the study.

Results of Plasma Insulin Studies with a FRI-1/Metformin Combination

Figure 2:
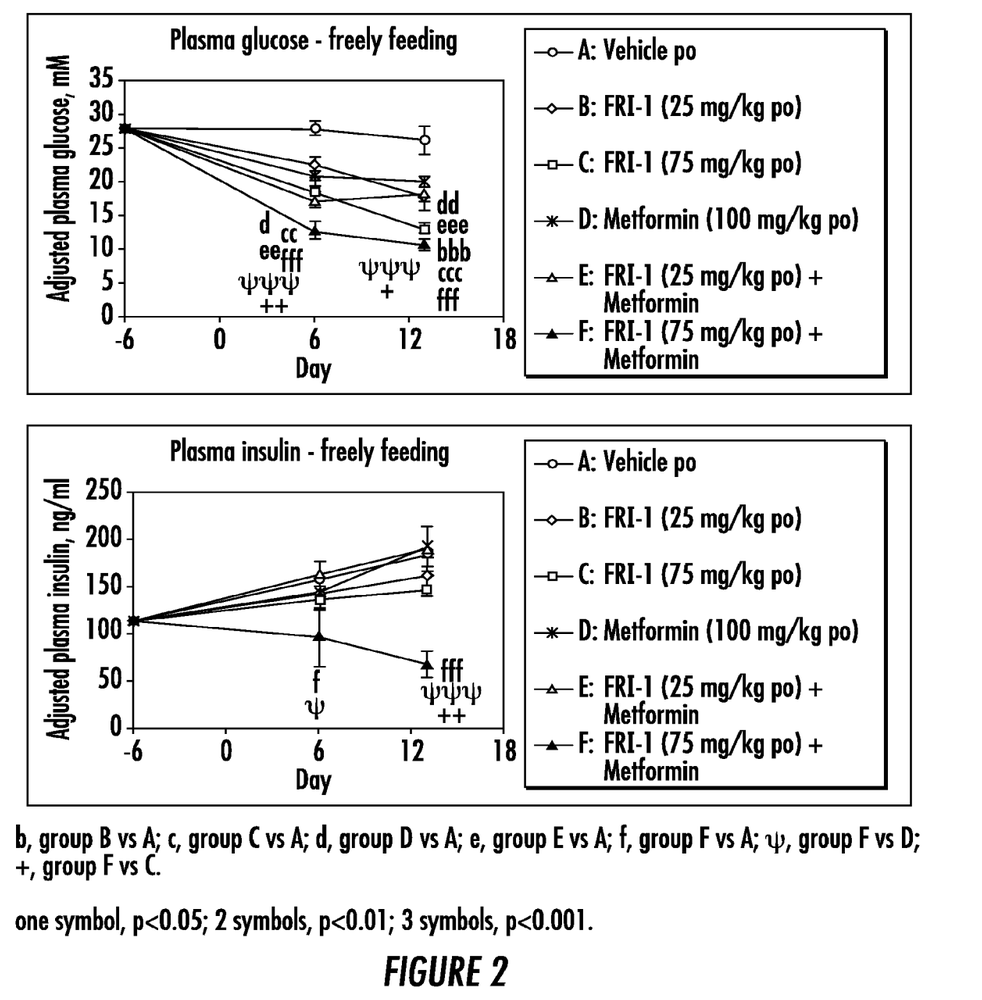
FIG. 2 depicts pharmacological effects of a combination of FRI-1 and metformin on plasma glucose and insulin in male ob/ob mice.
Figure 3:
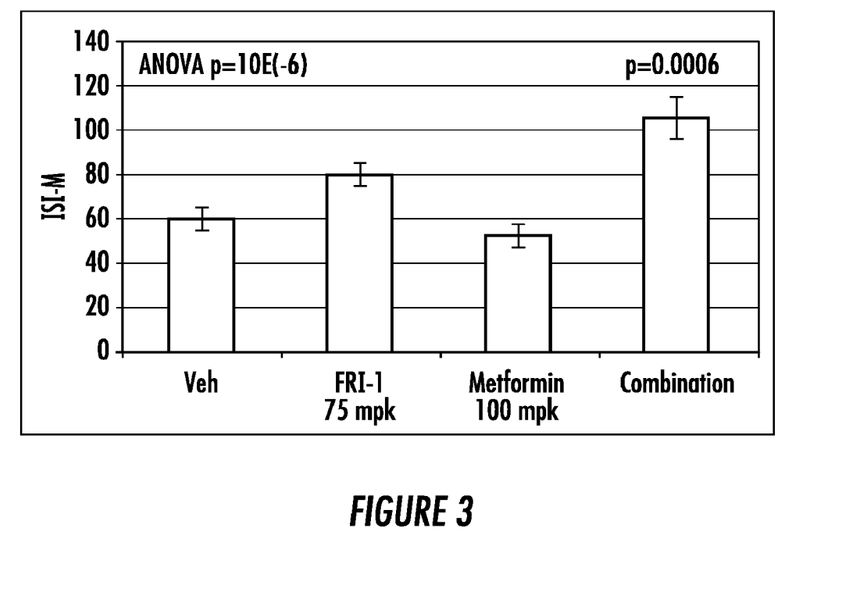
FIG. 3 depicts synergistic effects of a combination of FRI-1 and metformin on increasing insulin sensitivity as measured by the insulin sensitivity index (ISI).

Plasma insulin was determined from freely feeding ob/ob mice. The chronic administration of FRI-1 and metformin showed a synergistic effect on increasing insulin sensitivity as shown in FIGS. 2 and 3. In vehicle-treated animals, plasma insulin increased from a baseline level of approximately 110 ng/mL to 180 ng/mL on Day 13. The high dose FRI-1 and metformin combination had a significant effect on plasma insulin. Specifically, this combination treatment significantly reduced plasma insulin on Day 6 (p>0.05) and Day 13 (p<0.001). This reduction in insulin was significantly different not only to the levels of vehicle-treated controls but also to the Day 13 insulin levels of animals treated with either 75 mg/kg FRI-1 (p<0.01) or metformin (p<0.001) alone.

Results of Body Weight Studies with a FRI-1/Sitagliptin Combination

Figure 4:
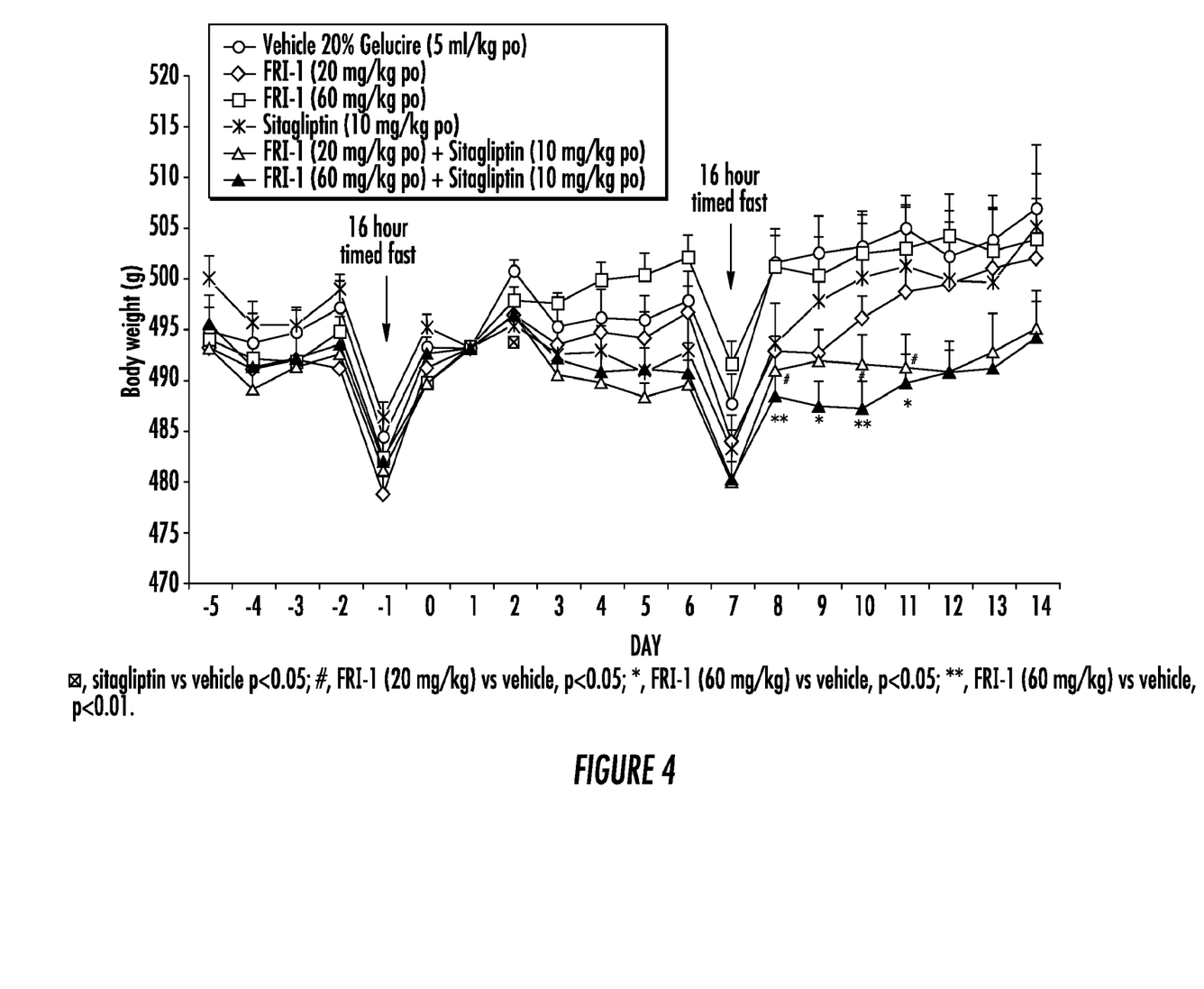
FIG. 4 depicts synergistic effects of a combination of FRI-1 and sitagliptin on body weight reduction in female diet-induced obese rats.

The chronic administration of FRI-1 and sitagliptin showed a synergistic effect on controlling body weight in female diet-induced obese rats as shown in FIG. 4.

Results of Plasma Insulin Studies with a FRI-1/Exenatide Combination

Figure 5:
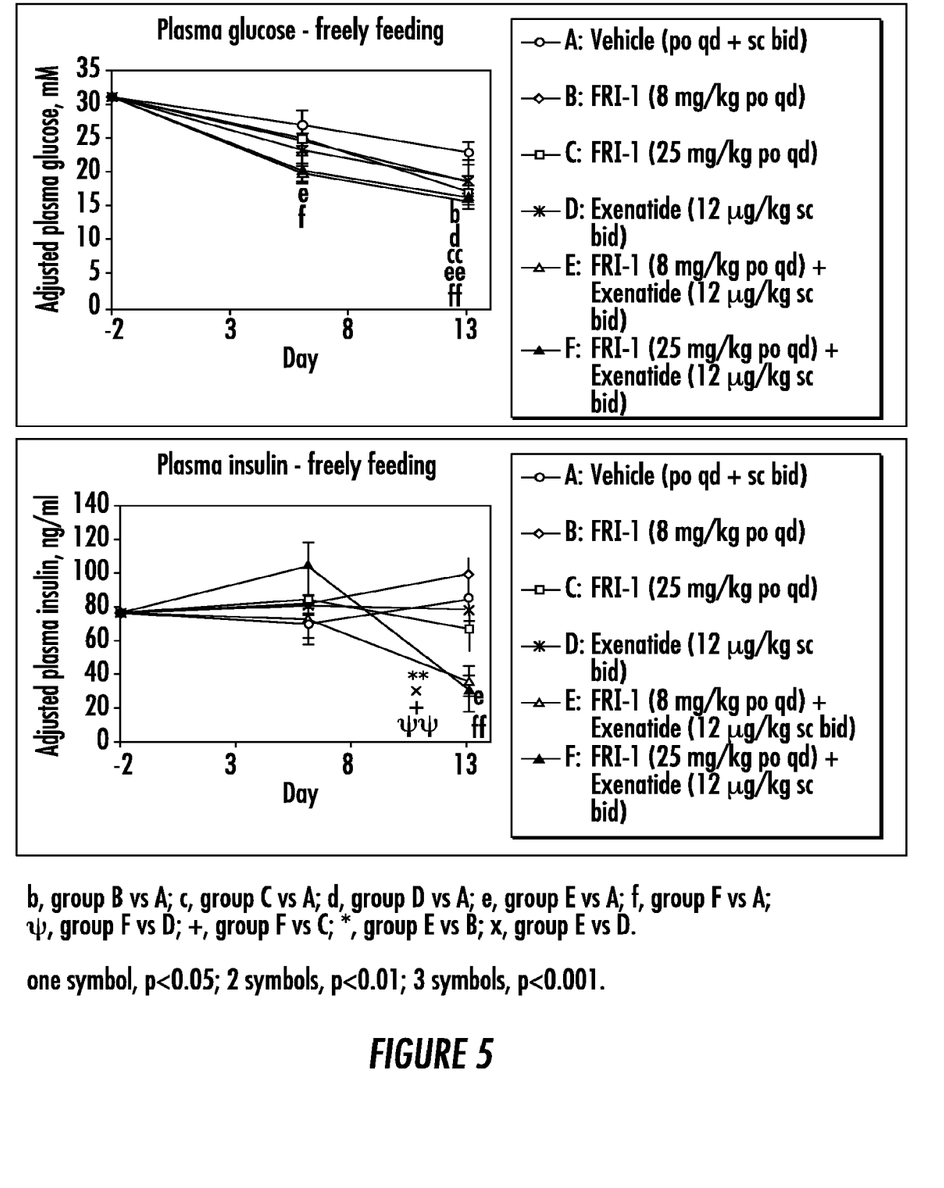
FIG. 5 depicts pharmacological effects of a combination of FRI-1 and exenatide on plasma glucose and insulin in male ob/ob mice.
Figure 6:
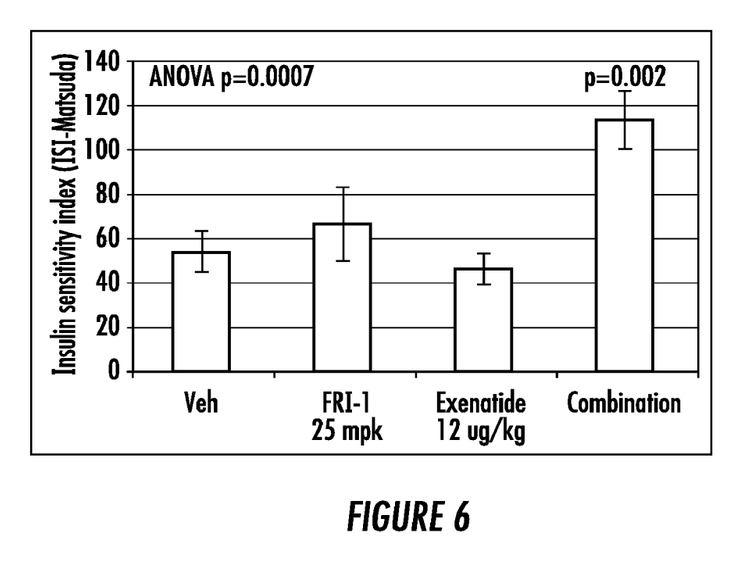
FIG. 6 depicts synergistic effects of a combination of FRI-1 and exenatide on increasing insulin sensitivity as measured by the insulin sensitivity index.

The chronic administration of FRI-1 and exenatide in ob/ob mice showed a synergistic effect on increasing insulin sensitivity as shown in FIGS. 5 and 6. Small but significant effects of exenatide and the combination of exenatide plus FRI-1 (25 mg/kg po) were observed to reduce plasma glucose on Day 7 when compared to vehicle. There were also significant effects of exenatide and the combination of exenatide plus both doses of FRI-1 (25 mg/kg po) to reduce plasma insulin on Day 7 when compared to vehicle. Extra statistical comparisons indicated that the effects of both combinations to reduce plasma insulin Day 14 were significantly greater than the effect of either dose of FRI-1 alone.

What is claimed is:

1. A method of reducing glycosylated hemoglobin HbA1c in a mammal by increasing the mammal's insulin sensitivity comprising:
    administering to the mammal a therapeutically effective amount of a liver-selective glucokinase activator in combination with a therapeutically effective amount of a GLP-1 analog or a pharmaceutically acceptable salt thereof,
    wherein the mammal has inadequate glycemic control.

2. The method of claim 1, wherein the mammal is a human.

3. The method of claim 2, wherein the human has a baseline HbA1c value from about 7.5% to about 15%.

4. The method of claim 2, wherein the amount of HbA1c is reduced by at least 0.3 percentage points.

5. The method of claim 1, wherein the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

6. The method of claim 1, wherein the liver-selective glucokinase activator and the GLP-1 analog are administered in discrete dosage forms.

7. The method of claim 6, wherein the GLP-1 analog is administered by injection and the liver-selective glucokinase activator is administered orally.

8. The method of claim 1, wherein the liver-selective glucokinase activator and the GLP-1 analog are administered in a single dosage form.

9. The method of claim 1, wherein the GLP-1 analog is exenatide or a pharmaceutically acceptable salt thereof.

10. A method of reducing glycosylated hemoglobin HbA1c in a human by increasing the human's insulin sensitivity comprising:
    administering to the human a therapeutically effective amount of a liver-selective glucokinase activator in combination with a therapeutically effective amount of a GLP-1 analog or a pharmaceutically acceptable salt thereof,
    wherein the human has impaired glucose metabolism,
    wherein the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

11. The method of claim 10, wherein the human has a baseline HbA1c value from about 7.5% to about 15%.

12. The method of claim 10, wherein the amount of HbA1c is reduced by at least 0.3 percentage points.

13. The method of claim 12, wherein the amount of HbA1c is reduced by at least 0.4 percentage points.

14. The method of claim 10, wherein the liver-selective glucokinase activator and the GLP-1 analog are administered in discrete dosage forms.

15. The method of claim 14, wherein the GLP-1 analog is administered by injection and the liver-selective glucokinase activator is administered orally.

16. The method of claim 10, wherein the liver-selective glucokinase activator and the GLP-1 analog are administered in a single dosage form.

17. The method of claim 10, wherein the GLP-1 analog is exenatide or a pharmaceutically acceptable salt thereof.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic Construct

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```